(12) United States Patent
Ohi et al.

(10) Patent No.: US 8,981,307 B2
(45) Date of Patent: Mar. 17, 2015

(54) PULSE HEIGHT ANALYZER AND NUCLEAR MEDICINE DIAGNOSIS APPARATUS PROVIDED WITH THE SAME

(75) Inventors: Junichi Ohi, Kyoto (JP); Tetsuo Furumiya, Kyoto (JP); Hiroyuki Takahashi, Tokyo (JP); Kenji Shimazoe, Tokyo (JP)

(73) Assignees: Shimadzu Corporation, Kyoto (JP); The University of Tokyo, Tokyo (JP)

( * ) Notice: Subject to any disclaimer, the term of this patent is extended or adjusted under 35 U.S.C. 154(b) by 421 days.

(21) Appl. No.: 13/499,320

(22) PCT Filed: Oct. 1, 2009

(86) PCT No.: PCT/JP2009/005081
§ 371 (c)(1),
(2), (4) Date: Mar. 30, 2012

(87) PCT Pub. No.: WO2011/039819
PCT Pub. Date: Apr. 7, 2011

(65) Prior Publication Data
US 2012/0184848 A1    Jul. 19, 2012

(51) Int. Cl.
*G01T 1/20* (2006.01)
*G01T 1/164* (2006.01)

(52) U.S. Cl.
CPC .................................. *G01T 1/1647* (2013.01)
USPC ........................................................ 250/369

(58) Field of Classification Search
CPC .................................................... G01T 1/1642
USPC ........................................................ 250/369
See application file for complete search history.

(56) References Cited

U.S. PATENT DOCUMENTS

2008/0001884 A1*   1/2008   Eames ............................ 345/92

FOREIGN PATENT DOCUMENTS

JP          2008-224609 A        9/2008

OTHER PUBLICATIONS

Research report of Next Generation PET 2008, "A prosect of PET appartus development (26); Application of Time overthreshold method in fornt-end signal processing" —Mar. 1, 2009—National Insititute of Radiological Sciences.
Work shop of Next Generation PET 2008, "A prosect of Pet appartus development (26); Application of Time overthreshold method in fornt-end signal processing" —Jan. 19, 2009—National Insititute of Radiological Sciences.

* cited by examiner

*Primary Examiner* — David Porta
*Assistant Examiner* — Hugh H Maupin
(74) *Attorney, Agent, or Firm* — McDermott Will & Emery LLP

(57) ABSTRACT

With a pulse-height analyzer, a reference-pulse generator generates a reference pulse of a given pulse height for a given period of time when an analog radiation pulse inputted to a comparator is higher than an initial threshold. A capacitor and a resistor receive the reference pulse, and then increase an increment threshold for the given period of time from the initial threshold to the given pulse height. Then the increment threshold is set as a reference voltage of the comparator. A pulse time width of the analog radiation pulse is determined through measuring a period of time from timing where the analog radiation pulse exceeds the initial threshold to timing where the analog radiation pulse being attenuated falls below the increment threshold.

11 Claims, 11 Drawing Sheets

PULSE HEIGHT ANALYZER AND NUCLEAR MEDICINE DIAGNOSIS APPARATUS PROVIDED WITH THE SAME

CROSS REFERENCE TO RELATED APPLICATIONS

This application is a U.S. National Stage application under 35 U.S.C. §371, of International Application PCT/JP2009/005081 filed on Oct. 1, 2009, which was published as WO 2011/039819 A1 on Apr. 7, 2011. The application is incorporated herein by reference.

TECHNICAL FIELD

This invention relates to a pulse height analyzer for analyzing a pulse height of a radiation pulse and taking out only a radiation pulse with a necessary pulse height. More particularly, this invention is directed to a technique of measuring a pulse height of a radiation pulse.

BACKGROUND ART

Three examples of such conventional pulse height analyzer are to be cited for description of a pulse height analyzer provided in a radiation detector. Here, a radiation pulse is obtained by converting emission due to interaction of incident gamma rays or X-rays on a scintillator into a current pulse by a photoelectric transducer, such as a PMT (Photomultiplier tube) and a photodiode, and further converting the current pulse into a voltage pulse via a current-to-voltage conversion circuit. Although the radiation pulses illustrated each differ in event, they are to be illustrated for convenience as having been detected at the same time.

The first technique is as below. That is, waveform shaping is performed on a radiation pulse having a pulse wavelength, as the sum of a rise time and a fall time of a pulse, of a few tens of nanoseconds with use of a filter (CR integration), until the pulse has a wavelength of a few microseconds. Then sample hold is performed on the radiation pulse when a given period of time (e.g., 500 nanoseconds) elapses after the radiation pulse on which the waveform shaping has been performed exceeds a threshold voltage. Then an analog-to-digital conversion is once performed on the peak value of the threshold voltage, whereby a pulse height is obtained (hereinafter, called a filter integration method.)

The second technique is as below. That is, waveform shaping is performed on a radiation pulse having a pulse wavelength of a few tens of nanoseconds with use of a filter (CR integration) until the pulse has a wavelength of a few hundreds nanoseconds. Then an analog-to-digital conversion is performed for eight times at intervals of a given period of time (e.g., 20 nanoseconds) after the radiation pulse on which the waveform shaping has been performed exceeds a threshold voltage. Then all pulse heights obtained through the analog-to-digital conversion are added to determine a pulse height of the radiation pulse, whereby a pulse height of the radiation pulse is obtained (hereinafter, called a digital integration method.)

The third technique is as follows. That is, waveform shaping is performed on a radiation pulse having a pulse wavelength of a few tens of nanoseconds with use of a filter (CR integration) until the pulse has a wavelength of a few hundreds nanoseconds. Then a pulse-time width is determined from when the radiation pulse on which waveform shaping has been performed exceeds a threshold voltage until it returns to the same threshold voltage, whereby a pulse height is obtained (hereinafter, called TOT (Time Over Threshold) method.) See, for example, Hiroyuki Takahashi, Takeshi Fujiwara, Kenji Shimazoe "A prospect of PET apparatus development (26); Application of Time over threshold method in front-end signal processing" NIRS-R (National Inst. of Radiological Sciences) National Institute of Radiological Sciences, Apr. 8, 2009. http://jglobal.jst.go.jp/public/20090422/200902256578352763

The conventional techniques, however, have the following drawbacks. Specifically, in the digital integration method, an analog-to-digital conversion is performed on the peak value of a radiation pulse for determining a pulse height. Accordingly, an analog-to-digital converter with high precision is required. Moreover, in the digital integration method, an analog-to-digital conversion is performed for eight times at intervals of 20 nanoseconds, for example, to determine each pulse height. Then all pulse heights are added to determine a pulse height. Accordingly, an analog-to-digital converter with an extremely high-speed is required. Both the analog-to-digital converters are expensive. Consequently, the number of analog-to-digital converters increases for use of individual analog-to-digital conversion of the radiation pulse successively outputted from the radiation detector that is formed of many radiation detecting elements, which results in huge costs. Moreover, since the processing and the control circuit are complicated, these techniques are not suitable for multi-channel applications.

In the TOT method, a pulse time width is determined, whereby a pulse height is determined. Thus, an analog-to-digital converter is not needed. Accordingly, the method may achieve an extremely simple configuration, and is also suitable for multi-channel applications. On the other hand, as illustrated in FIG. 10, linearity of the pulse time width relative to the pulse height becomes lower as the pulse height becomes higher. For instance, FIG. 11A illustrates radiation pulses Pa4, Pa5, and Pa6 after waveform-shaped. Here, a pulse time width of the radiation pulse Pa4 (a pulse time width from when the pulse exceeds the threshold voltage vth until returns to the threshold voltage vth) is Wtot4. A pulse time width of the radiation pulse Pa5 is Wtot5, and a pulse time width of the radiation pulse Pa6 is Wtot6. In comparison of pulses of high pulse heights such as the radiation pulses Pa4, Pa5, and Pa6, there is not so much difference between the pulse time widths Wtot4, Wtot5, Wtot6, rather than the pulse heights. In other words, the pulse height to be determined has a reduced accuracy. Accordingly, the situation as illustrated in FIG. 11B may occur. That is, a radiation pulse Pah of a high pulse height (e.g., radiation pulse Pa4, Pa5) that is originally out of an energy window EW enters in error into the energy window EW (e.g., the energy window EW containing the radiation pulse Pa6.) As a result, scattered components enter into an energy spectrum Pat in the energy window EW, whereby an energy spectrum Paf with low accuracy is generated. Consequently, the lower accuracy of the pulse height cannot be improved even when correction is performed using a look-up table. Thus, the problem still remains that energy resolution gets worse.

This invention has been made having regard to the state of the art noted above, and its object is to provide a pulse height analyzer that allows improved linearity of a pulse height relative to a pulse time width as well as enhanced energy resolution.

SUMMARY

This invention is constituted as stated below to achieve the above object. A pulse height analyzer of this invention determines a pulse height of a radiation pulse, obtained by converting emission due to incidence of radiation, through measuring a period of time from timing where the radiation pulse exceeds a given timing threshold to where the radiation pulse is attenuated to fall below the given threshold, and analyzes the pulse height of the radiation pulse to take out only a radiation pulse of a necessary pulse height. The pulse height analyzer includes a threshold increasing device for increasing the given threshold in synchronization with the timing where the radiation pulse exceeds the given threshold and measuring a period of time until the radiation pulse falls below the increment given threshold.

According to the pulse height analyzer of this invention, a pulse height of a radiation pulse obtained by converting emission due to incidence of radiation is determined through measuring a period of time from timing where the radiation pulse exceeds a given threshold to timing where the radiation pulse is attenuated to fall below the given threshold. The pulse height of the radiation pulse is analyzed to take out only a radiation pulse of a necessary pulse height. The threshold increasing device increases the given threshold in synchronization with the timing where the radiation pulse exceeds the given threshold. In other words, the timing where the radiation pulse is attenuated to fall below the given threshold is timing where the radiation pulse falls below the given increment threshold. As a result, the timing where the radiation pulse is attenuated to fall below the given threshold is earlier compared with the conventional pulse height analyzer having a fixed given threshold. Accordingly, linearity of a pulse height relative to a pulse time width may be improved and energy resolution may be enhanced.

The pulse height analyzer of this invention includes an initial-threshold outputting device for outputting an initial threshold of a constant voltage as a reference voltage, a comparator for comparing the radiation pulse and the initial threshold, a reference-pulse generating device for generating a reference pulse of a given pulse height for a given period of time when the radiation pulse is higher than the initial threshold, and an increment-threshold outputting device for outputting to the comparator an increment-threshold as a reference voltage in response to the reference pulse, the increment threshold being increased from the initial threshold to the given pulse height for the given period of time.

According to the foregoing pulse height analyzer, firstly the comparator compares the initial threshold and the radiation pulse, the initial threshold being outputted from the initial-threshold outputting device as a reference voltage. Then the reference-pulse generating device generates a reference pulse of a given pulse height for a given period of time when the radiation pulse is higher than the initial threshold. The increment-threshold outputting device increases the increment threshold from the initial threshold to the given pulse height for the given period of time in response to the reference pulse. Then the increment-threshold outputting device outputs the increment threshold as a reference voltage to the comparator. Accordingly, the pulse height of the radiation pulse is determined through measuring a period of time from timing where the radiation pulse exceeds a given threshold to timing where the radiation pulse is attenuated to fall below the increased threshold. Consequently, linearity of a pulse height relative to a pulse time width may be improved and energy resolution may be enhanced. In addition to this, the increment threshold is continuously increased for a given time period where output of the reference pulse is turned ON. Thus, occurrence of chattering may be suppressed that is generated due to the radiation pulse lower than the reference voltage. The pulse height of the radiation pulse may be analyzed accurately.

Moreover, in the pulse height analyzer of this invention, the reference-pulse generating device having a capacitor and a resistor is a one-shot multivibrator circuit for generating a reference pulse of a given pulse height with a given time constant using output signals as a trigger that are outputted from the comparator. The increment-threshold outputting device is a CR circuit formed of a capacitor and a resistor, and increases the increment-threshold with a given time constant by starting charge in response to the reference pulse. Such configuration is preferable.

According to the foregoing pulse height analyzer, the reference pulse generating device generates the reference pulse via the one-shot multivibrator circuit. The increment-threshold outputting device increases the increment threshold via the CR circuit. Moreover, the pulse height of the radiation pulse is determined through measuring a period of time from timing where the radiation pulse exceeds an initial threshold to timing where the radiation pulse is attenuated to fall below the increment threshold. Consequently, linearity of a pulse height relative to a pulse time width may be improved and energy resolution may be enhanced. In addition to this, no use of an analog-to-digital converter with high precision may achieve a pulse height analyzer of low price with simple processing and control circuit.

Moreover, the pulse height analyzer of this invention includes an increment-threshold decreasing device for decreasing the increment threshold to the initial threshold, and a threshold switching device for switching between the increment-threshold outputting device and the increment-threshold decreasing device. The threshold switching device switches to the increment-threshold outputting device in synchronization with rise of the reference pulse, and switches to the increment-threshold decreasing device in synchronization with fall of the reference pulse. Such configuration is preferable.

According to the foregoing pulse height analyzer, the increment-threshold decreasing device decreases the increment-threshold to the initial threshold. The threshold switching device switches between rise of the increment threshold by the increment-threshold outputting device and fall of the increment threshold by the increment-threshold decreasing device. The threshold switching device switches to increase the threshold in synchronization with rise of the reference pulse outputted at timing where radiation pulse exceeds the initial threshold, and switches to decrease the increment-threshold in synchronization with fall of the reference pulse. Consequently, linearity of a pulse height relative to a pulse time width may be improved, and energy resolution may be enhanced. In addition to this, the threshold switching device allows forced fall of the increment threshold. Accordingly, failure to determine the pulses may be suppressed even when more numbers of radiation pulses enter for a fixed period of time.

Nuclear medicine diagnosis apparatus of this invention includes a radiation detector and a pulse-height analyzer. The radiation detector converts radiation generated from a subject with radiopharmaceutical administered thereto into radiation pulses to detect the radiation. The pulse-height analyzer determines a pulse height of the radiation pulse through measuring a period of time from timing where the radiation pulse exceeds a given threshold to timing where the radiation pulse is attenuated to fall below the given threshold, and analyzes the pulse height of the radiation pulse to take out only a radiation pulse of a necessary pulse height. Nuclear medicine data of the subject is obtained based on the radiation pulses of the necessary pulse height taken out by the pulse height analyzer. The pulse-height analyzer includes a threshold increasing device for increasing the given threshold in synchronization with timing where the radiation pulse exceeds the given threshold and measuring a period of time until the radiation pulse falls below the increment given threshold.

According to the foregoing nuclear medicine diagnosis apparatus, the radiation detector converts radiation generated from a subject with radiopharmaceutical administered thereto into radiation pulses to detect the radiation. The pulse height of the radiation pulse is determined through measuring a period of time from timing where the radiation pulse exceeds a given threshold to timing where the radiation pulse is attenuated to fall below the given threshold, and the pulse height of the radiation pulse is analyzed to take out only a radiation pulse of a necessary pulse height. Nuclear medicine data of the subject is obtained based on the radiation pulses of the necessary pulse height taken out. Here, the threshold increasing device increases the given threshold in synchronization with timing where the radiation pulse exceeds the given threshold. In other words, the timing where the radiation pulse is attenuated to fall below the given threshold is timing where the radiation pulse falls below the increased given threshold. Thus, the timing where the radiation pulse is attenuated to fall below the given threshold is earlier compared with the conventional pulse height analyzer having a fixed given threshold. Accordingly, linearity of a pulse height relative to a pulse time width may be improved, and energy resolution may be enhanced. As a result, accuracy of the energy spectrum in a higher pulse height may be enhanced, and scattered components especially in high energy are removable. Consequently, nuclear medicine data with high diagnostic accuracy may be acquired.

Moreover, in the nuclear medicine diagnosis apparatus of this invention, the threshold increasing device includes an initial-threshold outputting device for outputting an initial threshold of a constant voltage as a reference voltage, a comparator for comparing the radiation pulse and the initial threshold, a reference-pulse generating device for generating a reference pulse of a given pulse height for a given period of time when the radiation pulse is higher than the initial threshold, and an increment-threshold outputting device for outputting to the comparator an increment-threshold as a reference voltage in response to the reference pulse, the increment threshold being increased from the initial threshold to the given pulse height for the given period of time. Such configuration is preferable.

According to the threshold increasing device in the foregoing nuclear medicine diagnosis apparatus, firstly the comparator compares the initial threshold and the radiation pulse, the initial threshold being outputted from the initial-threshold outputting device as a reference voltage. Then the reference-pulse generating device generates a reference pulse of a given pulse height for a given period of time when the radiation pulse is higher than the initial threshold. The increment-threshold outputting device increases the increment-threshold from the initial threshold to the given pulse height for the given period of time in response to the reference pulse. Then the increment-threshold outputting device outputs the increment-threshold as a reference voltage to the comparator. Accordingly, the pulse height of the radiation pulse is determined through measuring a period of time from timing where the radiation pulse exceeds a given threshold to timing where the radiation pulse is attenuated to fall below the increased threshold. Consequently, linearity of a pulse height relative to a pulse time width may be improved, and energy resolution may be enhanced. Thus, nuclear medicine data with high diagnostic accuracy may be acquired. In addition to this, the increment threshold is continuously increased for a given time period where output of the reference pulse is turned ON. Thus, occurrence of chattering may be suppressed that is generated due to the radiation pulse lower than the reference voltage. The pulse height of the radiation pulse may be analyzed accurately.

Moreover, in the nuclear medicine diagnosis apparatus of this invention, the reference-pulse generating device having a capacitor and a resistor is a one-shot multivibrator circuit for generating a reference pulse of a given pulse height with a given time constant using output signals as a trigger that are outputted from the comparator. The increment-threshold outputting device is a CR circuit formed of a capacitor and a resistor, and increases the increment threshold with a given time constant by starting charge in response to the reference pulse. Such configuration is preferable.

According to the foregoing nuclear medicine diagnosis apparatus, the reference pulse generating device generates the reference pulse via the one-shot multivibrator circuit. The increment-threshold outputting device increases the increment-threshold via the CR circuit. Moreover, the pulse height of the radiation pulse is determined through measuring a period of time from timing where the radiation pulse exceeds an initial threshold to timing where the radiation pulse is attenuated to fall below the increment threshold. Consequently, linearity of a pulse height relative to a pulse time width may be improved, and energy resolution may be enhanced. Thus, nuclear medicine data with high diagnostic accuracy may be acquired. In addition to this, the pulse height analyzer does not adopt an analog-to-digital converter with high precision, and processing and the control circuit thereof is simple. Consequently, there may be provided nuclear medicine diagnosis apparatus of low price and simple configuration.

Moreover, the nuclear medicine diagnosis apparatus of this invention includes an increment-threshold decreasing device for decreasing the increment threshold to the initial threshold through discharging the capacitor forcibly, and a threshold switching device for switching between the increment-threshold outputting device and the increment-threshold decreasing device. The threshold switching device switches to the increment-threshold outputting device in synchronization with rise of the reference pulse, and switches to the increment-threshold decreasing device in synchronization with fall of the reference pulse. Such configuration is preferable.

According to the foregoing nuclear medicine diagnosis apparatus, the increment-threshold decreasing device decreases the increment threshold to the initial threshold. Moreover, the threshold switching device switches between rise of the increment threshold by the increment-threshold outputting device and fall of the increment threshold by the increment-threshold decreasing device. The threshold switching device switches to the increment-threshold outputting device in synchronization with rise of the reference pulse outputted at a time where the radiation pulse exceeds the initial threshold, and switches to the increment-threshold decreasing device in synchronization with fall of the reference pulse. Consequently, linearity of a pulse height relative to a pulse time width may be improved, and energy resolution may be enhanced. Thus, nuclear medicine data with high diagnostic accuracy may be acquired. In addition to this, the threshold switching device allows for a drop of the increment threshold. Accordingly, failure to determine the pulses may be suppressed even when additional radiation pulses enter for a fixed period of time.

Moreover, in the nuclear medicine diagnosis apparatus of this invention, the radiation detector has a plurality of detector cells being arranged that are formed of scintillator elements and photoelectric transducers. Each detector cell has the comparator, the reference-pulse generating device, and the increment-threshold outputting device being arranged. According to the foregoing nuclear medicine diagnosis apparatus, the radiation detector has a plurality of detector cells being arranged that are formed of scintillator elements and photoelectric transducers. Each detector cell has the comparator, the reference-pulse generating device, and the increment-threshold outputting device being arranged. Thereby, even when the number of detector cells increases to increase the number of channels and the number of the pulse height analyzers to be used increases, the pulse height analyzer not using an analog-to-digital converter with high precision is of low price, and processing and the control circuit thereof is simple. Consequently, there may be provided nuclear medicine diagnosis apparatus of low price and simple configuration.

Moreover, the nuclear medicine diagnosis apparatus of this invention is a gamma camera that uses radiopharmaceutical labeled with radioisotope that emits a single photon, and varies at least one of a time constant used for the reference pulse generating device and a time constant used for the increment-threshold outputting device in accordance with intensity of the single photon.

According to the foregoing nuclear medicine diagnosis apparatus, when the gamma camera is adopted that uses radiopharmaceutical labeled with radioisotope that emits a single photon, at least one of a time constant used for the reference pulse generating device and a time constant used for the increment-threshold outputting device may be varied in accordance with intensity of the single photon. The gamma camera uses radiopharmaceutical labeled with radioisotope that emits a single photon. Thereby, even when the pulse height of the radiation pulse largely varies due to variation in drug to be used, and use of the pre-set increment-threshold does not lead to sufficient enhancement of linearity of a pulse height relative to a pulse time width, variation to an optimal time constant in accordance with intensity of the single photon may sufficiently achieve improved linearity.

Moreover, the nuclear medicine diagnosis apparatus of this invention varies at least one of a time constant used for the reference pulse generating device and a time constant used for the increment-threshold outputting device in accordance with a counting rate of the radiation pulse.

According to the foregoing nuclear medicine diagnosis apparatus, at least one of a time constant used for the reference pulse generating device and a time constant used for the increment-threshold outputting device may be varied in accordance with a counting rate of the radiation pulse. Thereby, even when the number of radiation pulses detected for a given period of time (counting rate) varies, and use of the increment-threshold set in advance does not lead to sufficient enhancement of linearity of a pulse height relative to a pulse time width, variation to an optimal time constant in accordance with a counting rate may sufficiently achieve improved linearity.

According to the pulse height analyzer of this invention, a pulse height of a radiation pulse obtained by converting emission due to incidence of radiation is determined through measuring a period of time from timing where the radiation pulse exceeds a given threshold to timing where the radiation pulse is attenuated to fall below the given threshold. The pulse height of the radiation pulse is analyzed to take out only a radiation pulse of a necessary pulse height. The threshold increasing device increases the given threshold in synchronization with the timing where the radiation pulse exceeds the given threshold. As a result, the timing where the radiation pulse is attenuated to fall below the given threshold is earlier compared with the conventional pulse height analyzer having a fixed given threshold. Accordingly, linearity of a pulse height relative to a pulse time width may be improved, and energy resolution may be enhanced.

DETAILED DESCRIPTION

A pulse height analyzer determines a pulse height of a radiation pulse obtained by converting emission due to incidence of radiation through measuring a period of time from timing where the radiation pulse exceeds a given threshold to timing where the radiation pulse is attenuated to fall below the given threshold. The pulse height analyzer has realized an object to improve linearity of a pulse time width relative to a pulse height through increasing the given threshold in synchronization with the timing where the radiation pulse exceeds the given threshold and measuring a period of time until the radiation pulse falls below the increment given threshold.

Figure 1:
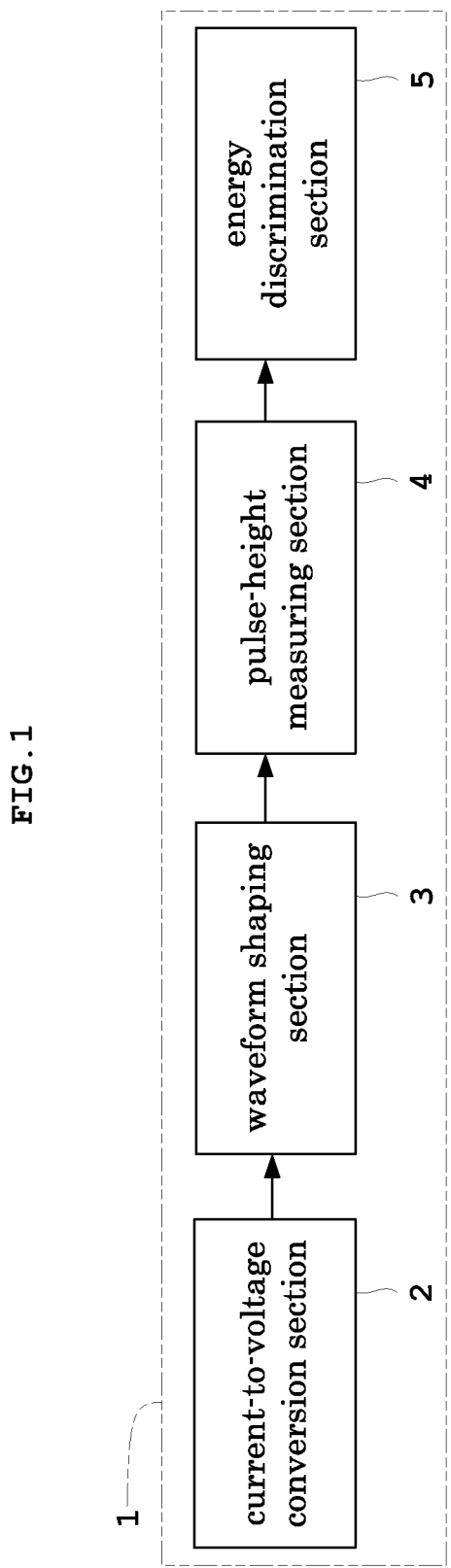
FIG. 1 is a block diagram showing an overall construction of a pulse-height analyzer according to an example.
Figure 2:
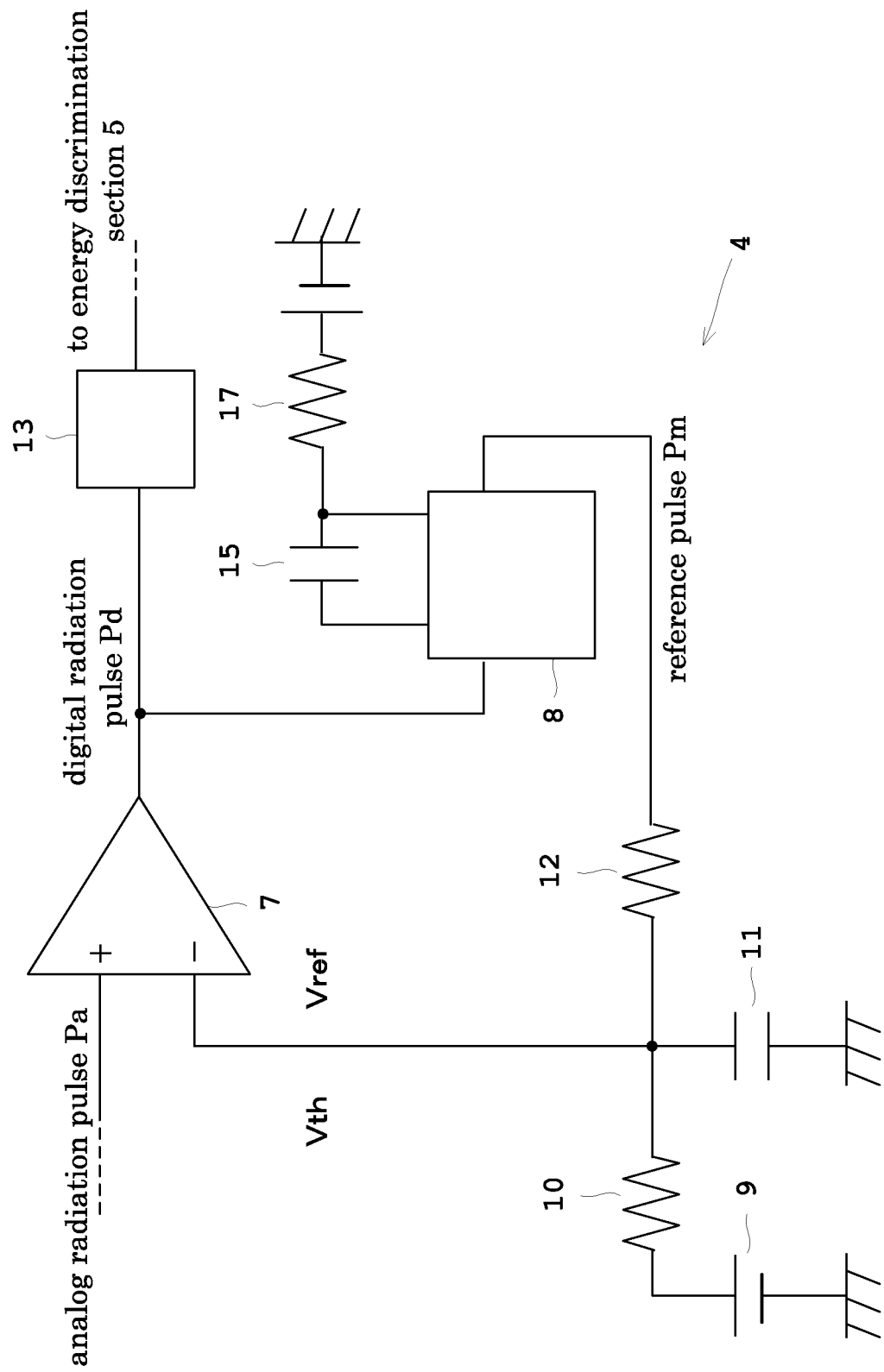
FIG. 2 is a circuit diagram of a pulse height measuring section provided for the pulse-height analyzer according to the example.
Figure 3:
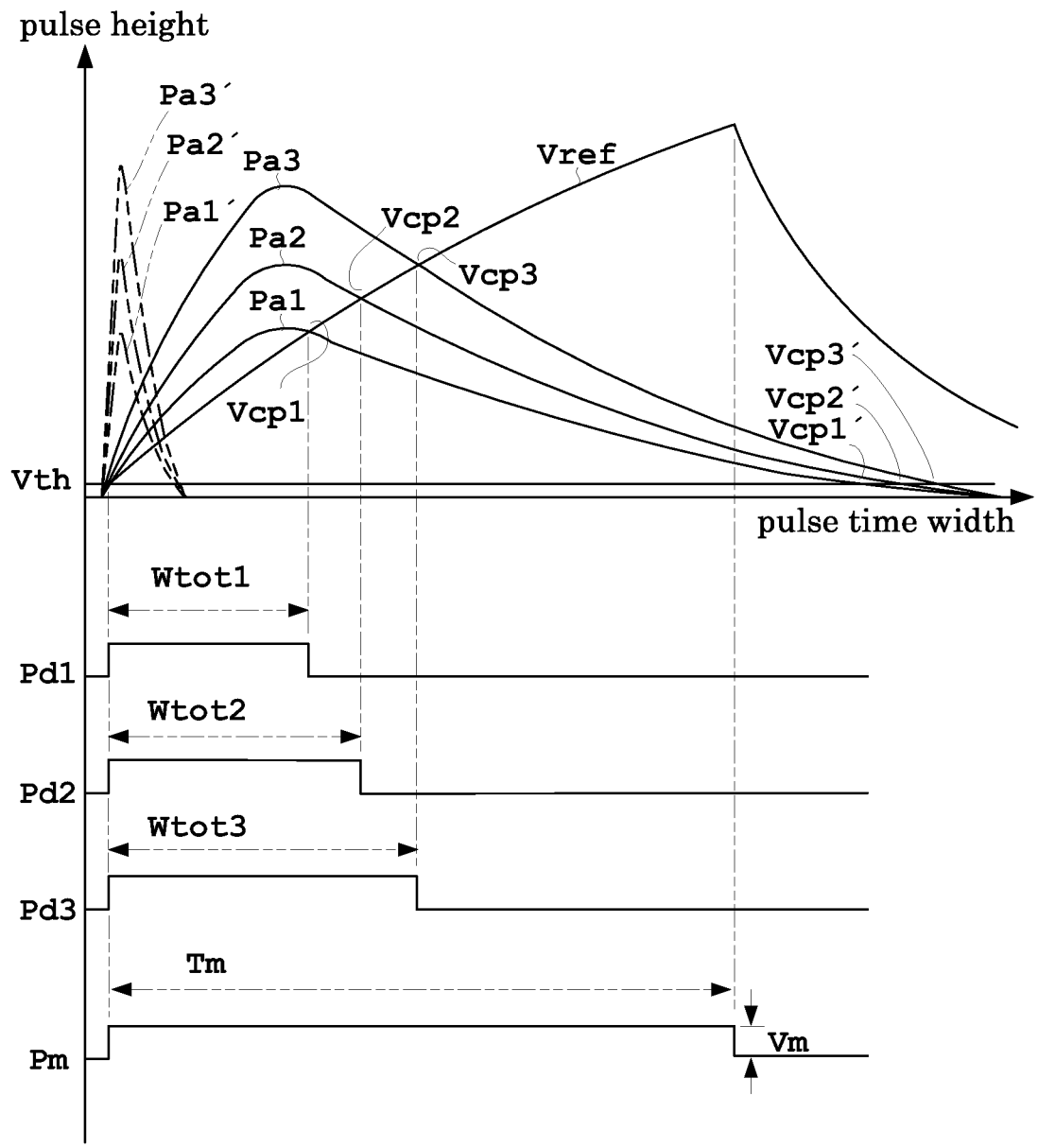
FIG. 3 is a timing chart showing increase of an increment threshold Vref in the pulse-height analyzer according to the example.
Figure 4:
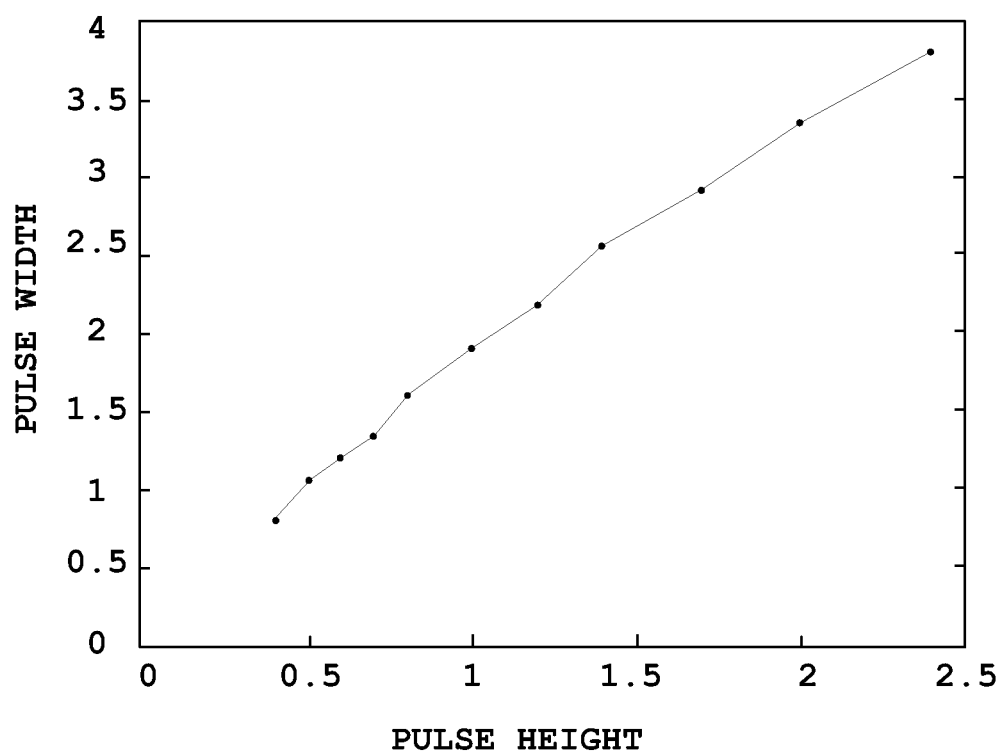
FIG. 4 is a line graph showing improvement of linearity of a pulse time width relative to a pulse height in the pulse height analyzer according to the example.

An example of this invention is described hereinafter with reference to the drawings. FIG. 1 is a block diagram showing an overall construction of a pulse-height analyzer according to the example. FIG. 2 is a circuit diagram of a pulse height measuring section that measures a pulse height of a radiation pulse. FIG. 3 is a timing chart showing increase of an increment threshold in the pulse-height measuring section. FIG. 4 is a line graph showing improvement of linearity of a pulse time width relative to a pulse height.

The overall construction of the example is described with reference to FIG. 1. A pulse height analyzer 1 according to the example includes a current-to-voltage conversion section 2 for converting a radiation pulse inputted as a current pulse into a voltage pulse, a waveform shaping section 3 for amplifying the radiation pulse converted into the voltage pulse to perform waveform shaping, a pulse-height measuring section 4 for measuring a pulse height of the waveform-shaped radiation pulse, and an energy discrimination section 5 for taking out only a radiation pulse of a given pulse height as a necessary pulse based on the pulse height.

The current-to-voltage conversion section 2 is formed of an operational amplifier that converts a radiation pulse inputted as a current pulse into a voltage pulse. A shaping amplifier provided with a CR integration circuit also allows performance of current-to-voltage conversion and waveform shaping in one circuit.

The waveform-shaping section 3 performs waveform shaping on radiation pulses with a filter such as a CR integration circuit. For instance, a radiation pulse having a pulse wave length of a few tens nanoseconds is integrated to be of a few hundreds nanoseconds, which is ten times thereof. Such waveform shaping is performed because an actual time from when a radiation pulse exceeds a threshold until it falls below the threshold (pulse time width) becomes much shorter compared with the pulse wave length of a few tens nanoseconds. It is also possible to measure a pulse time width without performing waveform shaping when a frequency of the counter pulse for measuring a pulse time width is set to be 1 GHz or more. In the apparatus used actually, however, it is difficult to output the pulse of such frequency. Accordingly, it is desirable to perform waveform shaping in order to measure a pulse time width by the counter pulse actually used with a frequency of 100 MHz through 200 MHz.

An electrical circuit constituting a pulse-height measuring section 4 will be described with reference to FIG. 2. The pulse-height measuring section 4 includes a comparator 7, a reference pulse generator 8, an initial threshold supply 9, a resistor 10, a capacitor 11 and a resistor 12, and a counter circuit 13. The comparator 7 compares an analog radiation pulse Pa on which waveform shaping is performed with an initial threshold Vth or an increment threshold Vref. The initial threshold Vth and the increment threshold Vref correspond to a reference voltage. The reference pulse generator 8 generates a reference pulse Pm of a given pulse height for a given period of time when the analog radiation pulse Pa is higher than the initial threshold Vth. The initial threshold supply 9 outputs the initial threshold Vth, corresponding to the reference voltage, to the comparator 7. The resistor 10 is connected between the initial threshold supply 9 and the comparator 7. The capacitor 11 and the resistor 12 are used for increasing the increment threshold Vref. The counter circuit 13 measures a pulse height of a digital radiation pulse Pd outputted from the comparator 7. Here, the comparator 7 corresponds to the comparator of this invention. The initial threshold supply 9 corresponds to the initial-threshold outputting device of this invention. The reference pulse generator 8 corresponds to the reference pulse generating device of this invention. The capacitor 11 and the resistor 12 correspond to the increment-threshold outputting device of this invention.

When a radiation pulse applied to a signal input (plus side) terminal exceeds a given threshold set in a reference voltage input (minus side), the comparator 7 turns output ON. When a radiation pulse falls below the given threshold set as the reference voltage, output is turned OFF. In other words, when an analog radiation pulse Pa exceeds the initial threshold Vth set as the reference voltage, the comparator 7 turns output of a digital radiation pulse Pd ON. When the analog radiation pulse Pa passes a peak value and falls below the increment threshold set as the reference voltage Vref while being attenuated, the comparator 7 turns output OFF. The comparator 7 outputs the digital radiation pulse Pd to the reference pulse generator 8 and the counter circuit 13.

The initial threshold Vth is of a fixed voltage value. The initial threshold Vth is preferably of a lower voltage value. That is because the higher a pulse height of a radiation pulse is, the shorter a period of time until the radiation pulse exceeds the initial threshold Vth becomes. Moreover, the lower the pulse height is, the longer a period of time until the radiation pulse exceeds the initial threshold Vth becomes. As a result, even if the radiation pulses of different pulse heights are measured simultaneously, a radiation pulse with a high pulse height has earlier timing of exceeding the initial threshold Vth. Then setting of the initial threshold Vth to be possibly low may achieve suppression of variations in such rise timing.

Then the reference-pulse generator 8 generates a reference pulse Pm of a given time width and a given pulse height at rise when a digital radiation pulse Pd is turned ON as a trigger. The reference pulse generator 8 is formed of a one-shot multivibrator circuit (monostable multivibrator circuit) having a capacitor 15 and a resistor 17. The reference pulse Pm is applied to the capacitor 11 and the resistor 12. The reference pulse generator 8 does not output another reference pulse Pm even when other pulses are inputted during turning ON to OFF of the reference pulse Pm. A given time width of the reference pulse Pm is determined by a time constant that is defined by the product of the capacity of the capacitor 15 and the value of the resistor 17 forming the reference pulse generator 8. The given pulse height of the reference pulse Pm is a fixed voltage value, such as 3.3v and 5v. The pulse height when the reference pulse Pm is OFF is the same voltage value as the initial threshold Vth.

The capacitor 11 accumulates electric charge during application of the reference pulse Pm to the capacitor 11. Accumulation of electric charge causes the capacitor 11 to increase the reference voltage set to the comparator 7. Thereby, the capacitor 11 increases the increment threshold for a given time width of the reference pulse Pm. The time constant determined by the product of the capacity of the capacitor 11 and the value of the resistor 12 is set in accordance with a period of time for increasing the increment threshold Vref, i.e., the given time width of the reference pulse Pm.

As above, when the reference pulse Pm is fed back as the reference voltage of the comparator 7 via the resistor 12 and the capacitor 11, the increment threshold Vref rises with time after exceeding the initial threshold Vth. The voltage value of the increment threshold Vref is determined by $Vm*(1-\exp(-t/\tau))$. Here, Vm is a pulse height of the reference pulse Pm, t is a period of time after the increment threshold Vref exceeds the initial threshold Vth, and $\tau$ is a time constant determined by the product of the capacity of the capacitor 11 and the value of the resistor 12. The increment threshold Vref increases exponentially as the value t becomes large, thereby being asymptotic to the pulse height Vm. Time until the increment threshold approaches the pulse height Vref becomes longer as the time constant $\tau$ becomes larger. Time until the increment threshold approaches the pulse height Vref becomes shorter as the time constant $\tau$ becomes smaller. Consequently, combination of the capacitor 11 and the resistor 12 may set the time constant τ freely within a range of the pulse time width Tm of the reference voltage Pm.

The counter circuit 13 measures the pulse time width of the digital radiation pulse Pd, thereby measuring the pulse height of the radiation pulse. That is, the counter circuit 13 generates a counter pulse synchronously with rise of the digital radiation pulse Pd, and stops the counter pulse synchronously with fall of the digital radiation pulse Pd. Then the pulse height of the radiation pulse is measured in accordance with the count number of the pulses counted during this period.

Next, operation of the circuit forming the pulse-height measuring section 4 is described. An analog radiation pulse Pa is inputted into the comparator 7. When the analog radiation pulse Pa is higher than the initial threshold Vth, the digital radiation pulse Pd is outputted to the reference pulse generator 8 and the counter circuit 13. The reference pulse generator 8 generates the reference pulse Pm, and applies voltage to the capacitor 11 and the resistor 12. The increment threshold Vref increases as the voltage applied to the capacitor 11 rises. When the analog radiation pulse Pa that is attenuated gradually is smaller than the increment threshold Vref, output of the digital radiation pulse Pd is turned OFF. The increment threshold Vref rises continuously even when output of the digital radiation pulse Pd is turned OFF. When the increment threshold Vref reaches a peak value, electric self-discharge will be started. The counter circuit 13 measures the pulse time width of the digital radiation pulse. Thereby, the pulse height of the analog radiation pulse Pa is measured.

Next, description will be given of timing where the increment threshold Vref increases with reference to FIG. 3. FIG. 3 is a timing chart in which the vertical axis represents the pulse height and the horizontal axis the pulse time width. Analog radiation pulses denoted by Pa1', Pa2', and Pa3' are outputted from the current-to-voltage conversion section 2. Analog radiation pulses denoted by Pa1, Pa2, and Pa3 are outputted from the waveform shaping section 3. Digital radiation pulses denoted by Pd1, Pd2, and Pd3 are outputted from the comparator 7. Pulse widths of Pd1, Pd2, and Pd3, are denoted by Wtot1, Wtot2, and Wtot3 respectively. A reference pulse denoted by Pm is outputted from the reference pulse generator 8. A pulse width of the reference pulse Pm is denoted by Tm. A pulse height of the reference pulse Pm is denoted by Vm. The increment threshold Vref increases so as to approach the pulse height Vm of the reference pulse.

Radiation pulses denoted by Pa1', Pa2', and Pa3' are inputted at different timings. Herein, for expediency of explanation, it is assumed that they start rising at the same time. The digital radiation pulse Pd1 rises synchronously with the time where the analog radiation pulse Pa1 exceeds the initial threshold Vth, and falls synchronously with the time where the analog radiation pulse Pa1 falls below the increment threshold Vref. The reference pulse Pm increases at rise of the digital radiation pulse Pd1 as a trigger, and falls after a given period of time Tm elapses. The increment threshold Vref further increases synchronously with rise of the reference pulse Pm. The increment threshold Vref increases beyond a cross point potential Vcp1 of the analog radiation pulse Pa1, and is attenuated synchronously with fall of the reference pulse Pm to be the initial threshold Vth. Pa2 and Pa3 are similar to Pa1, and thus explanation thereof is to be omitted for avoiding overlapping descriptions.

Cross point potentials Vcp1', Vcp2', Vcp3' of the analog radiation pulses Pa1, Pa2, Pa3 and the initial threshold Vth occur within a short period of time. On the other hand, the cross point potentials Vcp1, Vcp2, Vcp3 each have an interval of time sufficiently longer than the potentials Vcp1', Vcp2', Vcp3'. Moreover, the pulse time widths Wtot1, Wtot2, and Wtot3 each have a sufficient difference corresponding to the pulse heights of the analog radiation pulses Pa1, Pa2, and Pa3, respectively.

Description will be given of improvement of linearity of a pulse time width relative to a pulse height with reference to FIG. 4. FIG. 4 is a line graph in which the horizontal axis represents the pulse height and the vertical axis the pulse time width. It can be seen that the line graph conventionally has a gradient smaller as the pulse height became higher, but in this embodiment, it increases approximately linearly. Thus, it is proved that the linearity of the pulse time width relative to the pulse height may be improved.

According to the pulse height analyzer 1 described in this example, firstly the comparator 7 compares the initial threshold Vth and the analog radiation pulse Pa, the initial threshold Vth being outputted from the initial threshold supply 9 as a reference voltage. Then the reference-pulse generator 8 generates a reference pulse Pm of a given pulse height Vm for a given period of time Tm when the analog radiation pulse Pa is higher than the initial threshold Vth. The capacitor 11 and the resistor 12 receive the reference pulse Pm, and then increase the increment threshold Vref from the initial threshold Vth to the given pulse height Vm for the given period of time Tm. Then the increment-threshold Vref is set as a reference voltage of the comparator 7. Accordingly, the timing where the analog radiation pulse Pa is attenuated to fall below the given threshold is timing where the analog radiation pulse Pa falls below the increment threshold Vref. Thus, the pulse height of the analog radiation pulse Pa is determined through measuring a pulse time width from timing where the analog radiation pulse Pa exceeds an initial threshold Vrh to timing where the analog radiation pulse Pa is attenuated to fall below the increment threshold Vref. Accordingly, linearity of a pulse height relative to a pulse time width may be improved.

According to the pulse height analyzer 1 described in this example, the one-shot multivibrator circuit forming the reference pulse generator 8 generates the reference pulse Pm. The capacitor 11 and the resistor 12 increase the increment threshold Vref. Moreover, the pulse height of the radiation pulse is determined through measuring a period of time from timing where the analog radiation pulse Pa exceeds the initial threshold Vth to timing where the analog radiation pulse Pa is attenuated to fall below the increment threshold Vref. Consequently, linearity of a pulse height relative to a pulse time width may be improved, and energy resolution may be enhanced. In addition to this, no use of an analog-to-digital converter may achieve a pulse height analyzer of low price with simple processing and control circuit.

Figure 5:
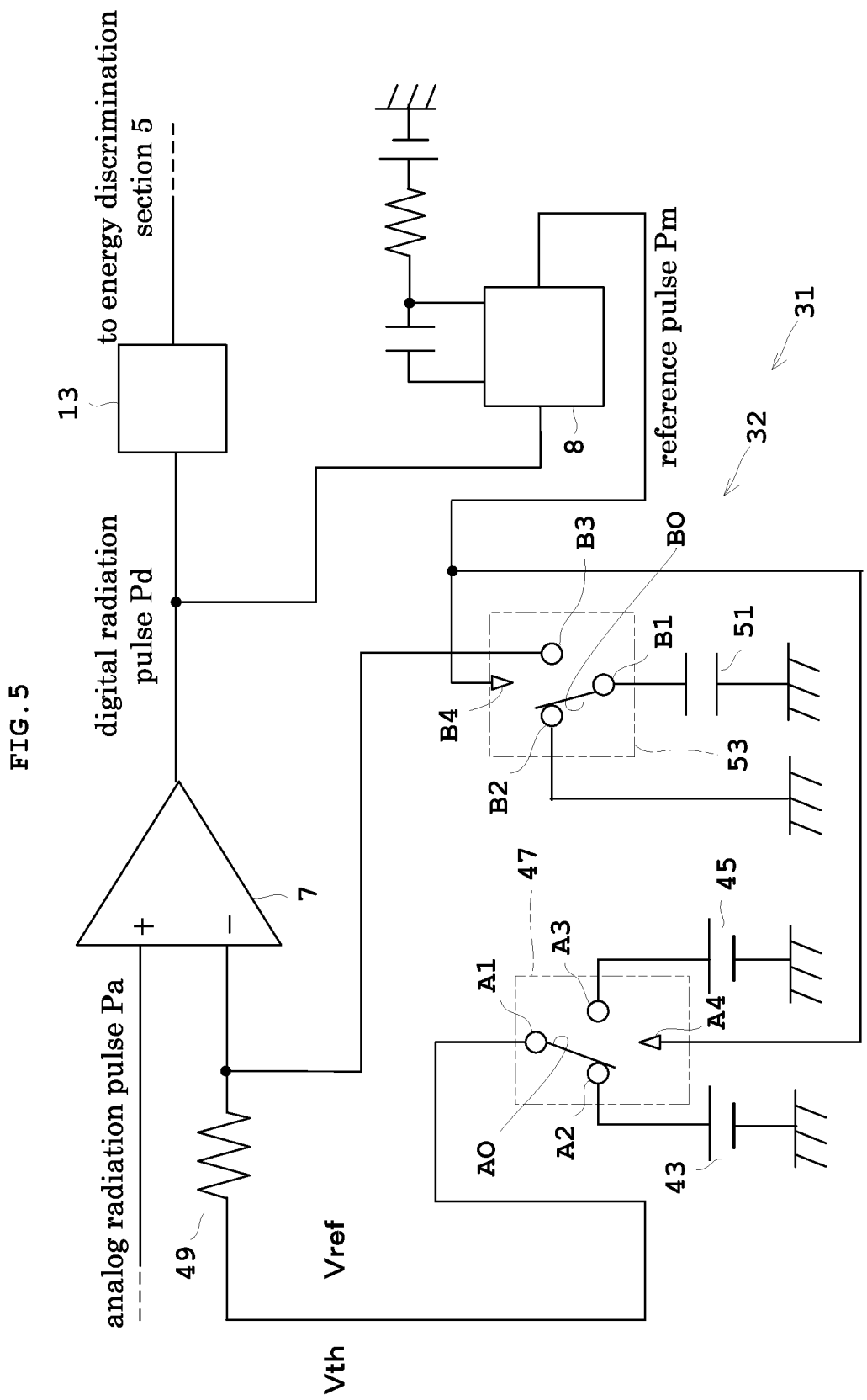
FIG. 5 is a circuit diagram of a pulse height measuring section 4 provided for a pulse-height analyzer according to another example.
Figure 6:
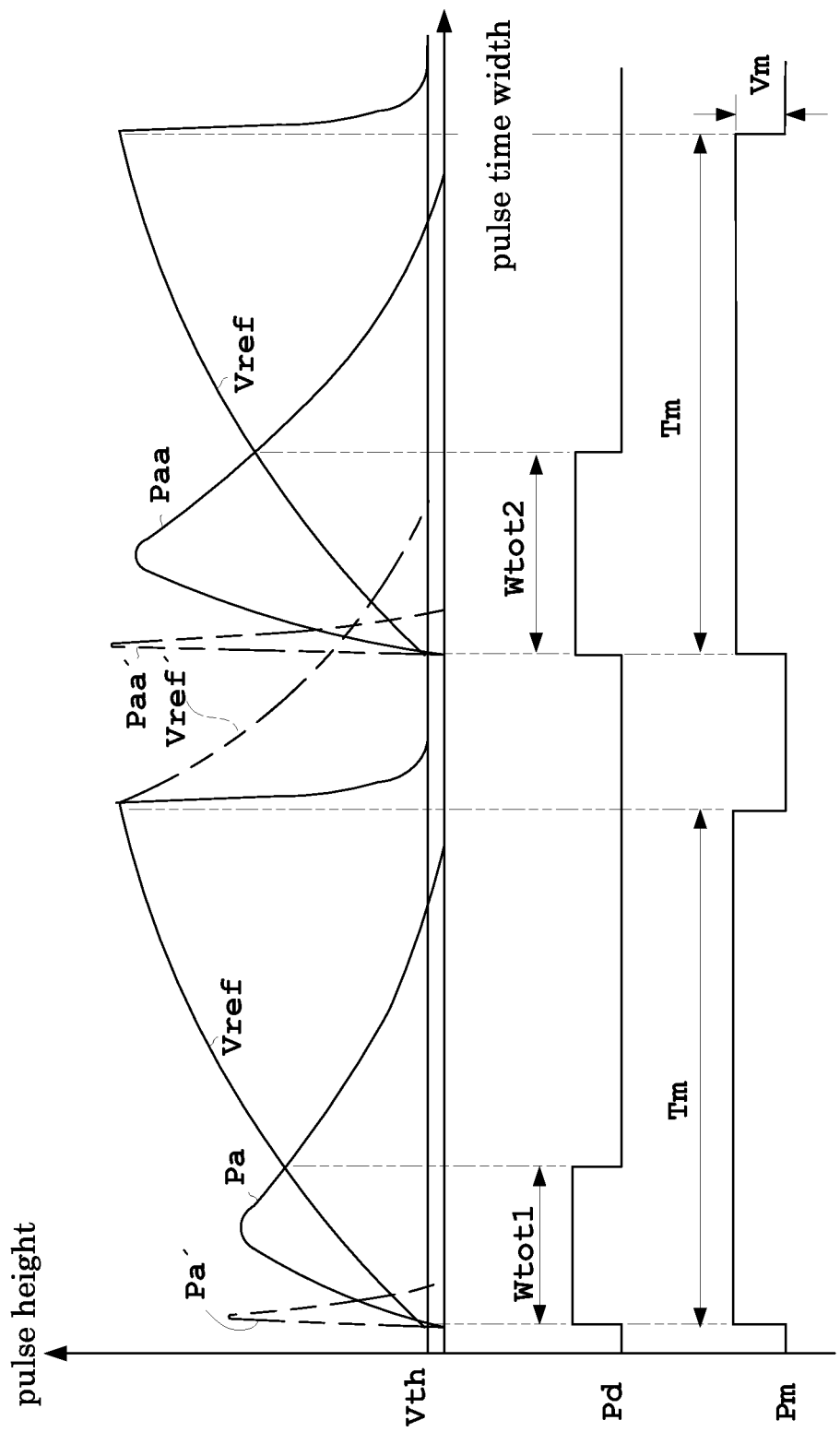
FIG. 6 is a timing chart showing rise and fall of an increment threshold in the pulse height analyzer according to the other example.

Next, another example of this invention is described with reference to the drawings. FIG. 5 is a circuit diagram of a pulse height measuring section provided in the pulse-height analyzer according to this other example for measuring a pulse height of a radiation pulse. FIG. 6 is a timing chart showing rise of an increment threshold used in the pulse height measuring section. Elements identical to those in the above example are to be described with the same reference numbers appropriately for avoiding overlapping descriptions.

A pulse-height measuring section 32 provided with a pulse height analyzer 31 according to this example includes a comparator 7, a counter circuit 13, a reference pulse generator 8, an initial threshold supply 43 for outputting reference voltage, an increment-threshold supply 45 for applying voltage to a resistor 49 and a capacitor 51 to be mentioned later, an analog switch 47 for switching between the initial threshold supply 43 and the increment-threshold supply 45, the resistor 49, the capacitor 51, and an analog switch 53 for switching between electric charge and discharge of the capacitor 51.

Here, other configuration except the pulse-height measuring section 32 are similar to those in the pulse height analyzer 1 according to the above example, and thus explanation thereof is to be omitted for avoiding overlapping descriptions.

The analog switch 47 is functionally formed of a common contact A1 having a switch lever AO, a contact A2 on an initial threshold supply 43 side, a contact A3 on an increment-threshold supply 45 side, and a switching section A4 for switching the switch lever AO between the contacts A2 and A3. The analog switch 53 is functionally, formed of a common contact B1 having a switch lever BO, a contact B2 on a discharge side, a contact B3 on a charge side, and a switching section B4 for switching the switch lever BO between the contacts B2 and B3. The capacitor 51 is connected to the common contact B1. Here, the switch lever BO, the common contact B1, and the contact B2 correspond to the increment-threshold decreasing device of this invention. The reference pulse generator 8 and the switching sections A4 and B4 correspond to the threshold switching device of this invention. The initial threshold supply 43, the switch lever AO, the common contact A1, and the contact A2 correspond to the initial-threshold outputting device. The increment-threshold supply 45, the switch lever AO, the common contact A1, the contact A3, the resistor 49, the contact B3, the common contact B1, the switch lever BO, and the capacitor 51 correspond to the increment-threshold outputting device.

Next, operation of the circuit forming the pulse-height measuring section 32 will be described. When no analog radiation pulse Pa is outputted, output of the comparator 7 is in an OFF state. Here, no digital radiation pulse Pd is inputted into the reference pulse generator 8. Accordingly, the reference pulse Pm is also OFF. Since the reference pulse Pm is OFF on the switch 47 side, the switch lever AO comes into contact with the contact A2. Accordingly, the comparator 7 and the initial threshold supply 43 are connected, and the reference voltage is the initial threshold Vth. Since the reference pulse Pm is OFF on the switch 53 side, the switch lever BO comes into contact with the contact B2. Accordingly electric charge accumulated in the capacitor 51 is sufficiently discharged. The switches 47 and 53 are maintained under this state after the analog pulse Pa is inputted until output of the comparator 7 is turned ON.

When the analog radiation pulse Pa is inputted into the comparator 7 to exceed the initial threshold Vth, output of the comparator 7 is turned into an ON state. At this time, the reference pulse generator 8 turns output of the reference pulse Pm ON in response to output of the comparator 7 turned ON. The switching section A4 on the switch 47 side switches in response to output of the reference pulse Pm turned ON. The switch lever AO of the common contact A1 comes into contact with the contact A3. The switching section B4 on the switch 53 side switches in response to output of the reference pulse Pm turned ON. The switch lever BO of the common contact B1 comes into contact with the contact B3. Accordingly, the increment-threshold supply 45, the resistor 49, and the capacitor 51 are electrically connected, and thus the capacitor 51 is charged. Then the increment threshold Vref rises to be as reference voltage.

When the analog radiation pulse Pa falls below the increment threshold Vref, output of the comparator 7 is turned OFF. On the other hand, the reference pulse Pm is kept ON for a period of time set in advance. Accordingly, the switches 47 and 53 are maintained under this state after the analog pulse Pa falls below the increment threshold Vref until a given period of time set in advance elapses.

When a given period of time set in advance elapses, the reference pulse generator 8 turns output of the reference pulse Pm OFF. The switching section A4 on the switch 47 side switches in response to output of the reference pulse Pm turned OFF. The switch lever AO of the common contact A1 again comes into contact with the contact A2. The initial threshold Vth is set as reference voltage. The switching section B4 on the switch 53 side switches in response to output of the reference pulse Pm turned OFF. The switch lever BO of the common contact B1 again comes into contact with the contact B2. Thereby, the capacitor 51 is forcibly discharged. The increment threshold Vref falls rapidly and reference voltage returns to the initial threshold Vth. When output of the comparator 7 is turns ON again and output of the reference pulse generator 8 is turned ON, the above operation is to be repeated.

Next, description will be given of timing where the increment threshold Vref increases with reference to FIG. 6. FIG. 6 is a timing chart in which the vertical axis represents a pulse height and the horizontal axis a pulse time width. Analog radiation pulses denoted by Pa' and Paa' are not waveform-shaped. Analog radiation pulses denoted by Pa' and Paa' are waveform-shaped. A digital radiation pulse denoted by Pd is outputted from the comparator 7. Pulse time widths of the digital radiation pulse Pd are denoted by Wtot1 and Wtot2. A reference pulse denoted by Pm is outputted from the reference pulse generator 8.

The digital radiation pulse Pd rises synchronously with timing where the analog radiation pulse Pa exceeds the initial threshold Vth, and falls synchronously with timing where the analog radiation pulse Pa falls below the increment threshold Vref. The reference pulse Pm increases at rise of the digital radiation pulse Pd as a trigger, and falls after a given period of time Tm elapses. The increment threshold Vref increases synchronously with rise of the reference pulse Pm, and is attenuated rapidly to the initial threshold Vth synchronously with fall of the reference pulse Pm.

Next, the digital radiation pulse Pd rises synchronously with the timing where the analog radiation pulse Paa exceeds the initial threshold Vth, and falls synchronously with the timing where the analog radiation pulse Paa falls below the increment threshold Vref. The reference pulse Pm increases at rise of the digital radiation pulse Pd as a trigger, and falls after a given period of time Tm elapses. The increment threshold Vref increases synchronously with rise of the reference pulse Pm, and is attenuated rapidly to the initial threshold Vth synchronously with fall of the reference pulse Pm.

Where it is supposed that the analog switch 53 is not provided that discharges the increment threshold Vref forcibly, the increment threshold Vref is self-discharged, which results in increment threshold Vref gradually falling like Vref'. Accordingly, when the analog radiation pulses Pa and Paa are inputted at relatively short time intervals, the increment threshold Vref' intersects the analog radiation pulse Paa. This may affect measurement of the pulse time width Wtot2 of the analog electrical pulse Paa. Rapid attenuation of the increment threshold Vref to the initial threshold Vth may achieve accurate measurement of the pulse time widths Wtot1 and Wtot2 of the analog radiation pulses Pa and Paa that are successively inputted.

According to the pulse height analyzer 31 of this example, the switch lever AO and the contact A3 of the common contact A1 are contacted and the switch lever BO and the contact B3 of a fulcrum B1 are contacted. Thereby, the increment threshold supply 45, the resistor 49, and the capacitor 51 are electrically connected. Accordingly, the increment threshold Vref increases as the voltage applied to the capacitor 51 rises. The switch lever AO and the contact A2 of the fulcrum A1 are contacted, thereby the reference voltage is set to be the initial threshold Vth. The switch lever B0 and the contact B2 of the fulcrum B1 are electrically contacted, thereby the increment threshold Vref falls forcibly to the initial threshold Vth. The analog switches 43 and 53 switch between rise and fall of the increment threshold Vref. The analog switches 43 and 53 switch to rise of the threshold in synchronization with rise of the reference pulse Pm outputted at timing where the radiation pulses Pa and Paa exceed the initial threshold, and switches to fall of the increment threshold in synchronization with fall of the reference pulse Pm. Accordingly, the analog switches 43 and 53 allow forced fall of the increment threshold Vref. Thus, linearity of the pulse height relative to the pulse time width may be improved, and failure to determine the radiation pulses may be suppressed even when more numbers of radiation pulses enter for a fixed period of time. That is because a possibility becomes lower that the increment threshold Vref used for measurement of the analog radiation pulse Pa intersects the analog radiation pulse Paa to be inputted subsequently.

Figure 7:
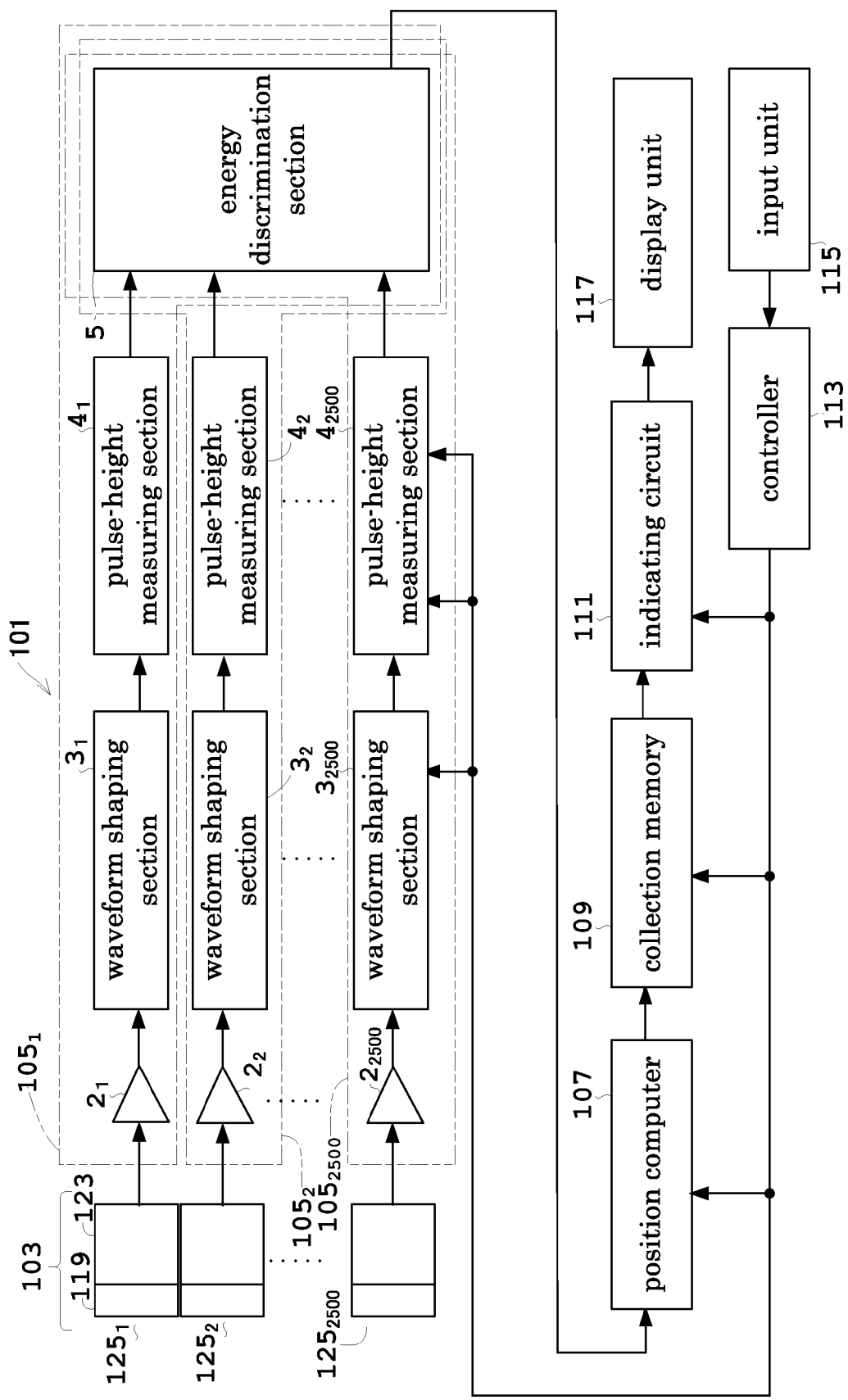
FIG. 7 is a block diagram showing an overall construction of a gamma camera according to a further example.
Figure 8:
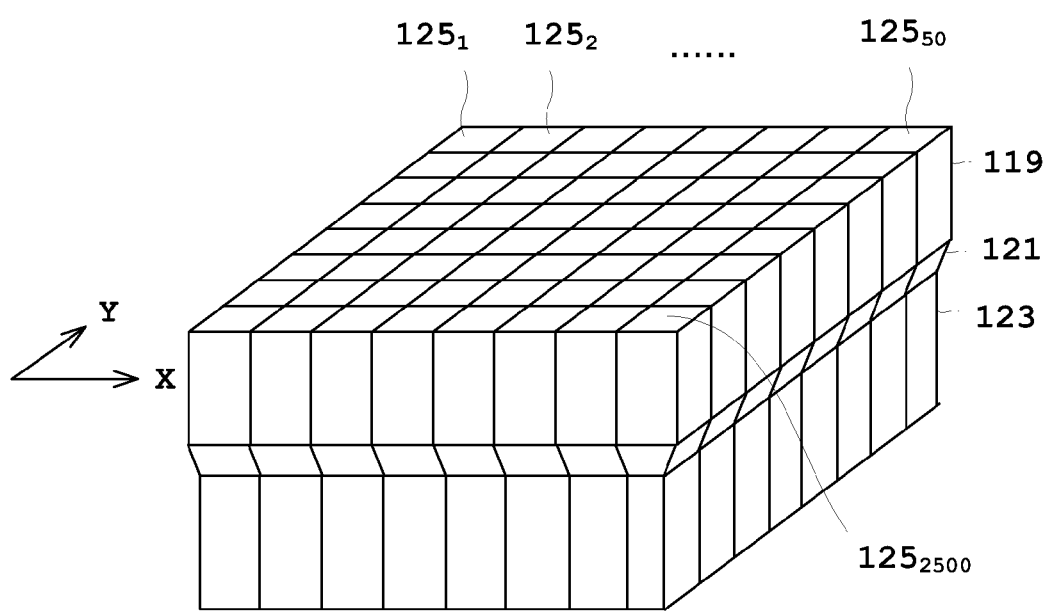
FIG. 8 is a schematic view of a gamma-ray detector provided for the gamma camera according to the further example.

Next, a further example of this invention is described with reference to the drawings. FIG. 7 is a block diagram showing an overall construction of a gamma camera 101 according to this example. FIG. 8 is a schematic view of a gamma-ray detector 103 provided for the gamma camera 101. Elements identical to those in above are to be described with the same reference numbers appropriately.

The gamma camera 101 includes a gamma-ray detector 103 for detecting gamma rays emitted from a subject with radiopharmaceutical administered thereto and outputting a current pulse, current-to-voltage conversion sections $2_1$ to $2_{2500}$ (which may be collectively called a current-voltage circuit 2), waveform-shaping sections $3_1$ to $3_{2500}$ (which may be collectively called a waveform-shaping section 3), pulse-height measuring sections $4_1$ to $4_{2500}$ (which may be collectively called a pulse-height measuring section 4), an energy discrimination section 5, a position computer 107 for calculating an incidence position of gamma rays, a collection memory 109 for writing and recording a count value of gamma rays into a memory corresponding to the incidence position, an indicating circuit 111 for reading data from the collection memory 109 and indicating it as a distribution image of radioisotope, a controller 113 for controlling these, an input unit 115 for inputting information necessary for control, and a display unit 117 for displaying the distribution image of radioisotope of the subject on a CRT or a paper medium. The current-to-voltage conversion section 2, the waveform-shaping section 3, the pulse-height measuring section 4, and the energy discrimination section 5 form the pulse height analyzer 105. Here, the gamma-ray detector 103 corresponds to the radiation detecting device of this invention. The gamma camera 101 corresponds to the nuclear medicine diagnosis apparatus of this invention.

The radiopharmaceutical administered to the subject is a drug labeled with radioisotope that emits single-photon gamma-rays, such as 99 mTc (Technetium) and 131I (Iodine).

Description will be given of the gamma-ray detector 103 with reference to FIG. 8. The gamma-ray detector 103 is a radiation detector or semiconductor detector formed of detector cells $125_1$ to $125_{2500}$ (which may be collectively called a detector cell 125) having a combination of a scintillator 119, a light guide 121 optically coupled to the scintillator 119, a photoelectric transducer 123 such as a photomultiplier tube (PMT) or Avalanche Photo Diode (APD).

The detector cell 125 has a two-dimensional array in X and Y directions. The detector cell 125 has 50 by 50 detector cells $125_1$ to $125_{2500}$ arranged in a two-dimensional matrix form in the X and Y directions. In this case, supposed that each detector cell 125 is square in shape and 1 mm in height and width, the gamma-ray detector 103 is square in shape and approximately 50 mm in height and width. One gamma-ray detector 103 is formed of 2500 detector cells. The pulse-height measuring section 4 included in the pulse height analyzer 1 of this invention is provided for every detector cell 125. Since the processing and the control circuit of the pulse-height measuring section 4 are not complicated, the pulse-height measuring section 4 may be downsized, and thus is applicable to the detector having multiple channels. Here, a PMT may also be used as the light-sensitive element 123, but it is desirable to use a semiconductor detector, such as an APD, in terms of miniaturization.

Next, description will be given of setting and variation of a time constant mentioned above. The time constant t may be set in accordance with intensity of the radiation pulse. Energy of the gamma rays emitted from radioisotope varies greatly depending on types of the radioisotope. For instance, energy of radiation emitted from 99 mTc is 141 keV, and energy of radiation emitted from 131I is 364 keV. Accordingly, where the time constant set for measuring energy of radiation from 99 mTc is set as it is for the time constant for measuring energy of radiation from 131I, there arises a possibility not to improve linearity of the pulse time width relative to the pulse height. In this case, the time constant τ is varied through changing the capacity of the capacitor 11 and the value of the resistor 12.

Moreover, the time constant τ may be set in accordance with a counting rate of a radiation pulse. As the number of radiation pulses inputted increases for a given period of time, it is necessary to measure a pulse height of one radiation pulse in as short a time as possible. In order to achieve this, it is necessary to shorten a period of time from timing where the analog radiation pulse Pa begins to be attenuated until timing where the analog radiation pulse Pa falls below the increment threshold Vref. It is also necessary to consider a period of time from when the voltage value of the capacitor 11 reaches a peak value until self-discharge is completed. When a counting rate of a radiation pulse is large in such case, the capacity of the capacitor 11 and the value of the resistor 12 may be reduced for decreasing the time constant τ.

According to the gamma camera 101 of this example, the comparator 7, the reference pulse generator 8, the capacitor 11, and the resistor 12 increase the given threshold in synchronization with timing where the radiation pulse Pa exceeds the given threshold. Thus, the pulse time width of the analog radiation pulse Pa is determined through measuring a period of time from timing where the analog radiation pulse Pa exceeds an initial threshold Vth to timing where the analog radiation pulse Pa falls below the increment threshold Vref. Here, the timing where the analog radiation pulse Pa is attenuated to fall below the given threshold Vref is earlier compared with the conventional pulse height analyzer having a fixed given threshold. Accordingly, linearity of a pulse height relative to a pulse time width may be improved, and energy resolution may be enhanced. As a result, accuracy of the energy spectrum in a higher pulse height may be enhanced, and scattered components especially in high energy are removable. Consequently, nuclear medicine data with high diagnostic accuracy may be acquired.

According to the gamma camera 101 of this example, firstly the comparator 7 compares the initial threshold Vth and the analog radiation pulse Pa, the initial threshold Vth being outputted from the initial-threshold supply 9 as a reference voltage. Then the reference-pulse generator 8 generates a reference pulse Pm of a given pulse height Vm for a given period of time Tm when the analog radiation pulse Pa is higher than the initial threshold Vth. The capacitor 11 and the resistor 12 receive the reference pulse Pm, and then increase the increment-threshold Vref from the initial threshold Vth to the given pulse height Vm for the given period of time Tm. Then the capacitor 11 outputs the increment threshold Vref as a reference voltage to the comparator 7. Accordingly, the pulse height of the analog radiation pulse Pa is determined through measuring a period of time from timing where the analog radiation pulse Pa exceeds a given threshold Vth to timing where the analog radiation pulse Pa is attenuated to fall below the increased threshold Vref. Consequently, linearity of a pulse height relative to a pulse time width may be improved, and energy resolution may be enhanced. Thus, nuclear medicine data with high diagnostic accuracy may be acquired. In addition to this, the increment threshold Vref is continuously increased for a given time period Tm where output of the reference pulse is turned ON. Thus, occurrence of chattering may be suppressed that is generated due to the analog radiation pulse Pa lower than the increment threshold Vref as the reference voltage. The pulse height of the radiation pulse may be analyzed accurately.

According to the gamma camera 101 of this example, the reference pulse generator 8 generates the reference pulse Pm via the one-shot multivibrator circuit. The capacitor 11 and the resistor 12 increase the increment threshold Vref via the CR circuit. The pulse height of the analog radiation pulse Pa is determined through measuring a period of time from timing where the analog radiation pulse Pa exceeds the initial threshold Vth to timing where the analog radiation pulse Pa is attenuated to fall below the increment threshold Vref. Consequently, linearity of a pulse height relative to a pulse time width may be improved, and energy resolution may be enhanced. Thus, nuclear medicine data with high diagnostic accuracy may be acquired. In addition to this, the pulse height analyzer 105 does not adopt an analog-to-digital converter and processing and the control circuit thereof is simple. Consequently, there may be provided nuclear medicine diagnosis apparatus of low price and simple configuration.

According to the gamma camera 101 of this example, the radiation detector 103 has a plurality of detector cells 125 being arranged that are formed of scintillator elements 119 and photoelectric transducers 123. Each detector cell 125 has the comparator 7, the reference-pulse generating device 8, the capacitor 11 and the resistor 12 being arranged. Thereby, even when the number of detector cells 125 increases to increase the number of channels and the number of the pulse height analyzers 105 to be used increases, the pulse height analyzer 105 not using an analog-to-digital converter with high precision is of low price, and processing and the control circuit thereof is simple. Consequently, there may be provided nuclear medicine diagnosis apparatus of low price and simple configuration.

According to the gamma camera 101 of this example, at least one of a time constant τ determined with the capacity of the capacitor 15 and the value of the resistor 17 that forms the reference-pulse generating device 8 and a time constant determined with the capacity of the capacitor 11 and the value of the resistor 12 is varied in accordance with intensity of a single photon outputted from radioisotope. Thereby, variation to an optimal time constant in accordance with intensity of the single photon may result in sufficiently improved linearity.

According to the gamma camera 101 of this example, at least one of a time constant τ determined with the capacity of the capacitor 15 and the value of the resistor 17 that forms the reference-pulse generating device 8 and a time constant determined with the capacity of the capacitor 11 and the value of the resistor 12 is varied in accordance with a counting rate of a radiation pulse. Thereby, variation to an optimal time constant in accordance with a counting rate of a radiation pulse may result in sufficiently improved linearity.

This invention is not limited to the foregoing examples, but may be modified as follows.

(1) In each of the foregoing examples, the reference pulse generating device 8 generates the reference pulse Pm at rise of the digital radiation pulse Pd as a trigger, and the increment threshold Vref is increased during application of the reference pulse Pm to the capacitors 11 and 51. This is not limitative. The digital radiation pulse Pd may be directly applied to the capacitors 11 and 51 without the reference pulse generator 8. The reason is as explained below. That is, in the TOT method, a pulse time width is determined from when a radiation pulse exceeds the threshold voltage until the radiation pulse returns to the equal threshold voltage. In contrast to this, the threshold voltage is increased after a radiation pulse exceeds the threshold voltage, and a pulse time width until the threshold voltage returns to the increment-threshold voltage is determined. Accordingly, the pulses of a high pulse height may have a pulse time width in accordance with the pulse height.

Figure 12:
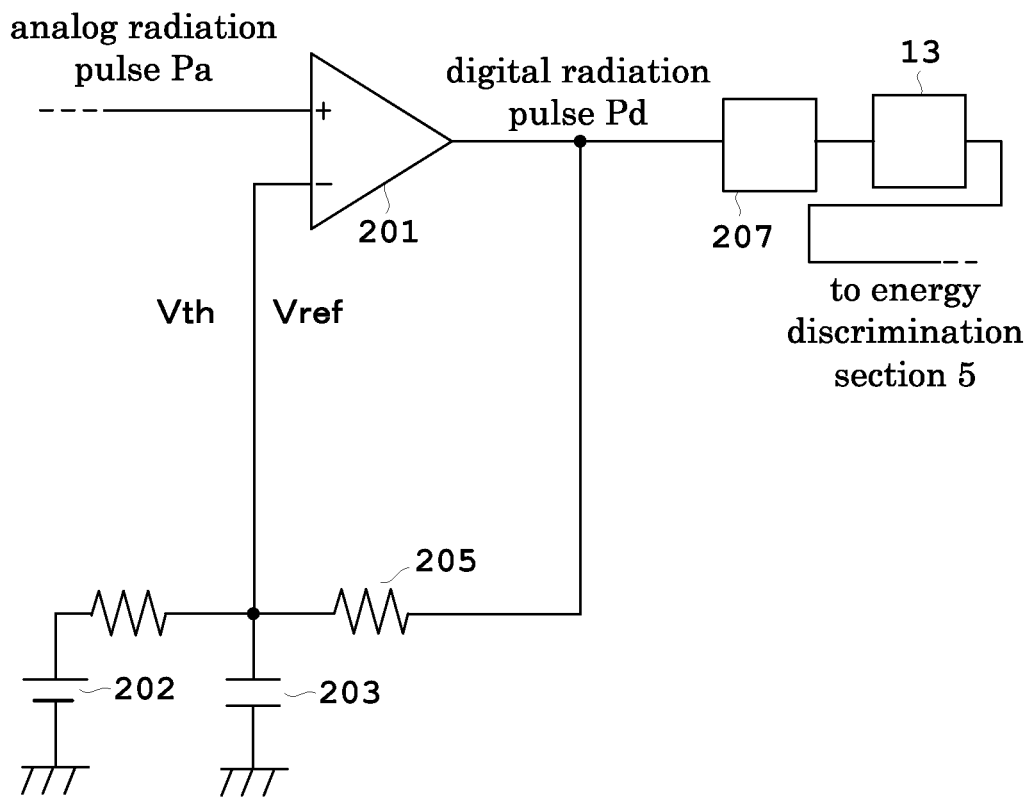
FIG. 12 is a conventional circuit diagram.
Figure 13:
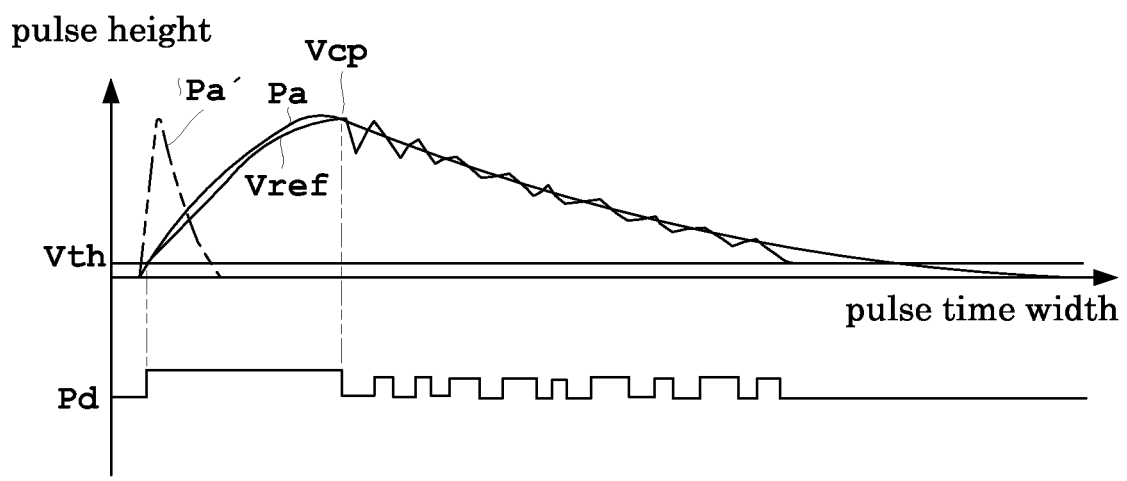
FIG. 13 is a timing chart showing the conventional chattering that occurs in the circuit diagram.

Description will be given of the foregoing modification with reference to FIGS. 12 and 13. FIG. 12 is a circuit diagram showing increase of an increment threshold Vref in the modification, and FIG. 13 is a timing chart thereof. An initial-threshold supply 202 applies an initial threshold Vth to a comparator 201 as reference-voltage input. A digital radiation pulse Pd outputted from the comparator 201 is fed back as a reference voltage via a capacitor 203 and a resistor 205 to the comparator 201. Thereby, the increment threshold Vref fed back gradually increases with a time constant as the product of the capacity of the capacitor 203 and the value of the resistor 205. Here, the capacitor 203 and the resistor 205 correspond to the increment-threshold outputting device of this invention.

The comparator 201, the initial-threshold supply 9, the reference pulse generator 8, the capacitor 11, and the resistor 12 increase the threshold Vref in synchronization with timing where the analog radiation pulse Pa exceeds the initial threshold Vth. That is, the timing where the analog radiation pulse Pa is attenuated to fall below the given threshold is timing where the analog radiation pulse Pa falls below the increment threshold Vref. Accordingly, the timing where the analog radiation pulse Pa is attenuated to fall below the increment threshold Vref is earlier than the timing where the analog radiation pulse Pa falls below the initial threshold Vth. Accordingly, linearity of a pulse height relative to a pulse time width may be improved.

The following problem naturally occurs in such a configuration, which is to be described with reference to FIG. 13. Specifically, the digital radiation pulse Pd outputted from the comparator 201 is directly fed back to the comparator 201, even via the capacitor 203 and the resistor 205. When the capacitor 203 is charged to a given reference voltage and is saturated, self-discharge is performed. On the other hand, output of the comparator 201 is turned OFF at the timing where the analog radiation pulse Pa falls below the increment threshold Vref. Accordingly, the increment threshold Vref rapidly falls rather than falls by self-discharge. When the radiation pulse exceeds the threshold voltage rapidly falling, output of the comparator is turned ON. Accordingly, the threshold voltage increases. Then output of the comparator is turned OFF again at the timing where the radiation pulse falls below the increment threshold voltage. Accordingly, the threshold voltage rapidly falls. As shown in FIG. 13 as above, chattering occurs after the analog radiation pulse Pa falls below the increment threshold Vref. Thus, numerous small oscillations are generated in the digital radiation pulse Pd, which may avoid measuring of the pulse time width.

Then, a filter circuit 207 is provided for performing filtering of the digital radiation pulse Pd outputted to the counter circuit 13. The filter circuit 207 is the so-called low-pass filter. That is, in FIG. 13, the higher a frequency is, the smaller an amplitude becomes. The chattering appears as high frequency components of the digital radiation pulse Pd. Then, oscillation due to chattering may be removed with use of the low-pass filter that cuts high frequency components across a given cutoff frequency. Thereby, even in the configuration where the increment threshold Vref is fed back to the comparator 201 by direct application of the digital radiation pulse Pd to the capacitors 11 and 51 without the reference pulse generator 8, the pulse height may be measured under a reduced influence to measurement of the pulse time width due to chattering.

(2) In each of the foregoing examples, the reference pulse generator 8 is a one-shot multivibrator circuit. Alternatively, it may be a digital-pulse generator that outputs a digital pulse of given pulse time width and pulse height synchronously with rise of the digital radiation pulse Pd.

Figure 9:
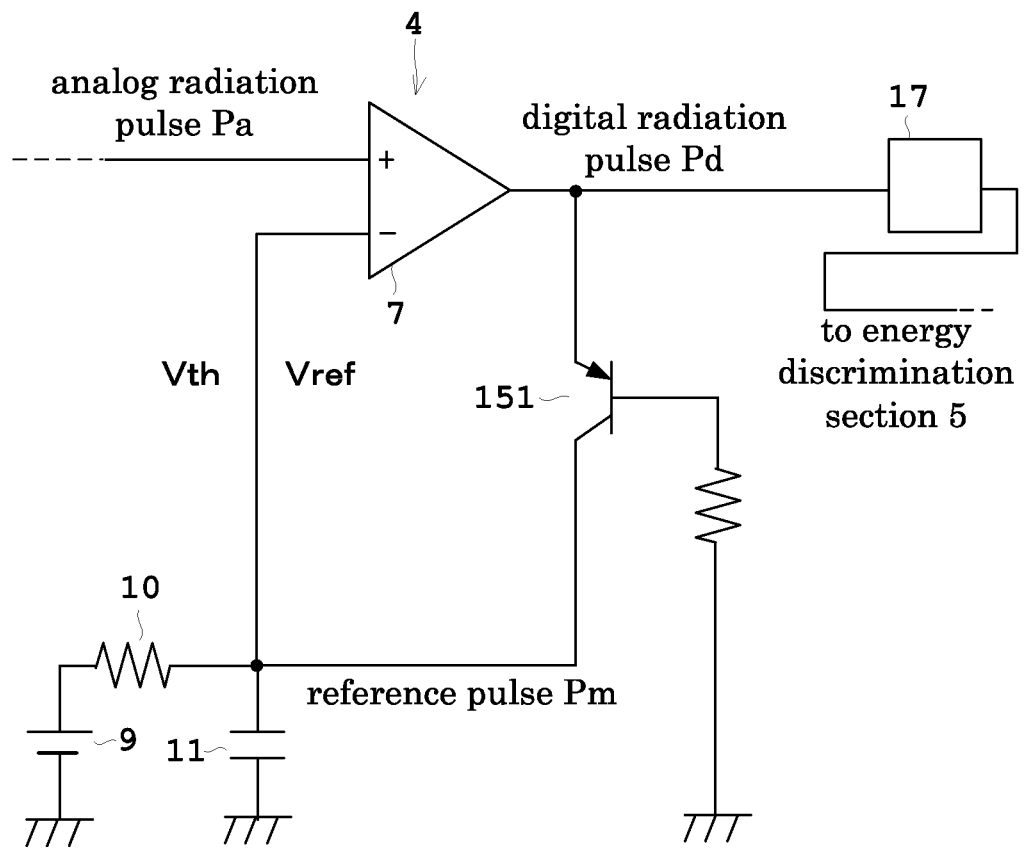
FIG. 9 is a circuit diagram showing a constant current circuit provided for the modification according to each example.
Figure 10:
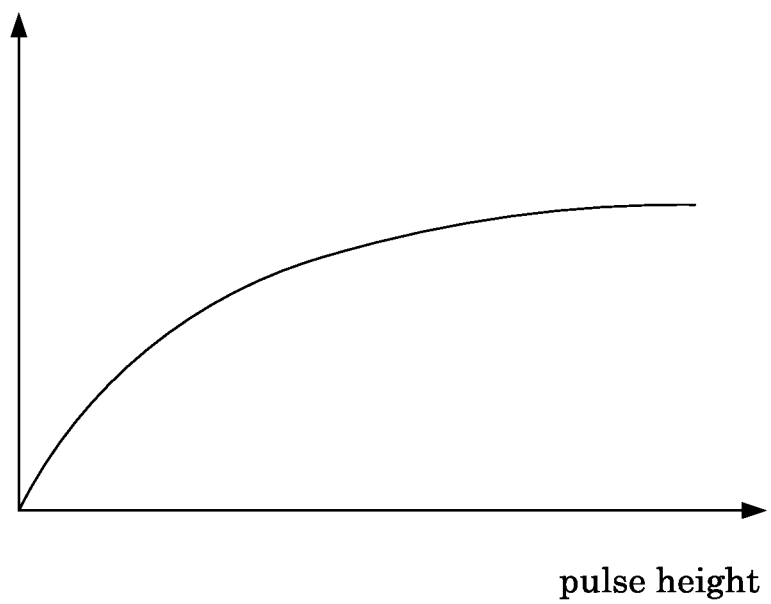
FIG. 10 is a schematic view showing a relation between a pulse height and a pulse time width in the conventional TOT method.
Figure 11A:
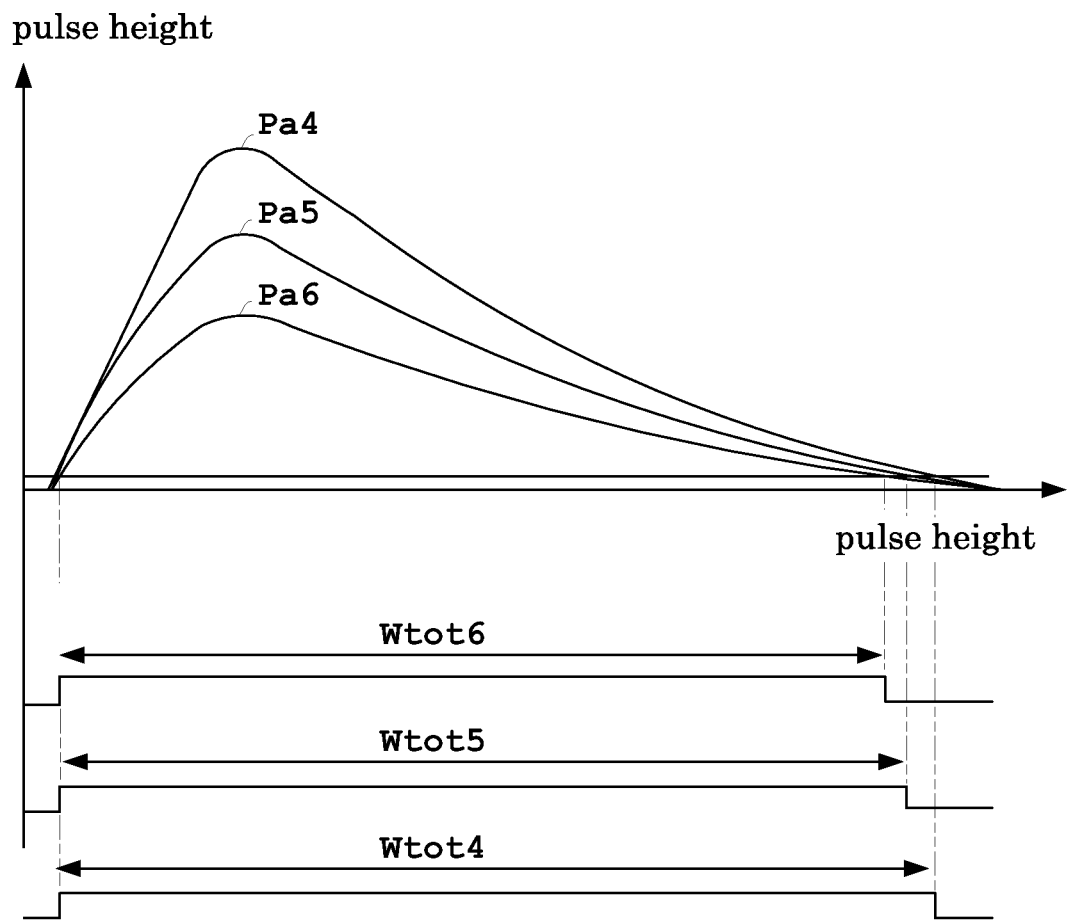
FIG. 11 is a timing chart in the conventional TOT method.
Figure 11B:
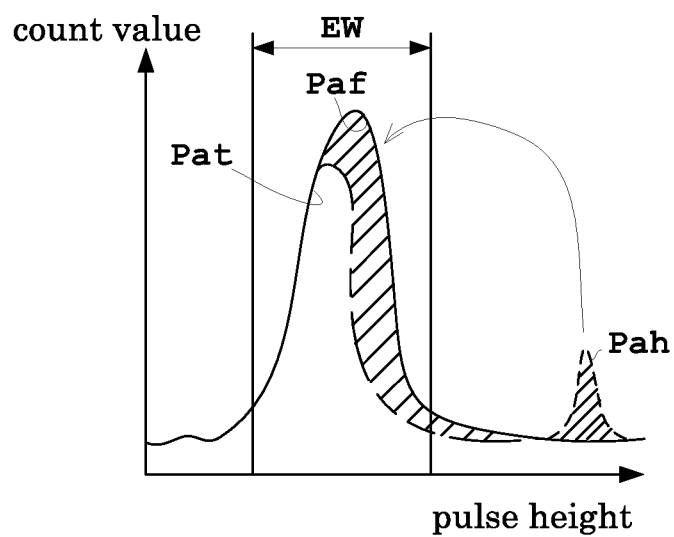

(3) In each of the foregoing examples, the reference pulse generator 8 is a one-shot multivibrator circuit. Alternatively, as shown in FIG. 9, it may be a constant current circuit formed of a transistor 151 for feeding given current for a given period of time synchronously with rise of the digital radiation pulse Pd.

(4) One of the foregoing examples includes the pulse height analyzer 1 according to another example as the pulse height analyzer 105. Alternatively, it may include the pulse height analyzer 31 according to a different example.

(5) In the foregoing example, the radiopharmaceutical is a drug labeled with the radioisotope emitting single-photon gamma-rays. Alternatively, the radiopharmaceutical may be drugs with a positron emitting nuclide.

(6) In the foregoing, the radiation detector 103 has 50 detector cells 125 arranged two-dimensionally in the X and Y direction, respectively. Alternatively, it may be a ring-type detector having block detectors formed of a plurality of detector cells 125 being arranged in a ring shape.

(7) In the foregoing example, the gamma camera 101 is adopted. Alternatively, SPECT apparatus with a mechanism for rotating the detector 103 around a body axis of a subject, or a PET device with the above-mentioned ring-type detector may be adopted.

As noted above, this invention is suitable for improvement of linearity of a pulse height relative to a pulse time width in the pulse height analyzer for detecting a pulse height of the radiation pulse through measuring a period of time from timing where the radiation pulse exceeds a given threshold to timing where the radiation pulse is attenuated to fall below the given threshold.

The invention claimed is:

1. A pulse height analyzer for determining a pulse height of a radiation pulse, obtained by converting emission due to incidence of radiation, through measuring a period of time from timing where the radiation pulse exceeds a given threshold to timing where the radiation pulse is attenuated to fall below the given threshold, and analyzing the pulse height of the radiation pulse to take out only a radiation pulse of a necessary pulse height, comprising:
a threshold increasing device increasing the given threshold in synchronization with the timing where the radiation pulse exceeds the given threshold and measuring a period of time until the radiation pulse falls below the increment given threshold.

2. A pulse height analyzer for determining a pulse height of a radiation pulse, obtained by converting emission due to incidence of radiation, through measuring a period of time from timing where the radiation pulse exceeds a given threshold to timing where the radiation pulse is attenuated to fall below the given threshold, and analyzing the pulse height of the radiation pulse to take out only a radiation pulse of a necessary pulse height, comprising:
an initial-threshold outputting device outputting an initial threshold of a constant voltage as a reference voltage;
a comparator comparing the radiation pulse and the initial threshold;
a reference-pulse generating device generating a reference pulse of a given pulse height for a given period of time when the radiation pulse is higher than the initial threshold; and
an increment-threshold outputting device outputting to the comparator an increment-threshold as a reference voltage in response to the reference pulse, the increment threshold being increased from the initial threshold to the given pulse height for the given period of time.

3. The pulse height analyzer according to claim 2, wherein the reference-pulse generating device having a capacitor and a resistor is a one-shot multivibrator circuit for generating a reference pulse of a given pulse height with a given time constant using output signals as a trigger that are outputted from the comparator, and
the increment-threshold outputting device is a CR circuit formed of a capacitor and a resistor, and increases the increment-threshold with a given time constant by starting charge in response to the reference pulse.

4. The pulse height analyzer according to claim 3, further comprising:
an increment-threshold decreasing device decreasing the increment threshold to the initial threshold through discharging the capacitor forcibly; and
a threshold switching device switching between the increment-threshold outputting device and the increment-threshold decreasing device,
wherein the threshold switching device switches to the increment-threshold outputting device in synchronization with rise of the reference pulse, and switches to the increment-threshold decreasing device in synchronization with fall of the reference pulse.

5. Nuclear medicine diagnosis apparatus comprising:
a radiation detector converting radiation generated from a subject with radiopharmaceutical administered thereto into radiation pulses to detect the radiation; and
a pulse-height analyzer determining a pulse height of the radiation pulse through measuring a period of time from timing where the radiation pulse exceeds a given threshold to timing where the radiation pulse is attenuated to fall below the given threshold, and analyzing the pulse height of the radiation pulse to take out only a radiation pulse of a necessary pulse height,
nuclear medicine data of the subject being obtained based on the radiation pulses of the necessary pulse height taken out by the pulse height analyzer, wherein
the pulse-height analyzer comprises a threshold increasing device increasing the given threshold in synchronization with timing where the radiation pulse exceeds the given threshold and measuring a period of time until the radiation pulse falls below the increment given threshold.

6. The nuclear medicine diagnosis apparatus according to claim 5, wherein
the threshold increasing device comprises:
an initial-threshold outputting device outputting an initial threshold of a constant voltage as a reference voltage;
a comparator comparing the radiation pulse and the initial threshold;
a reference-pulse generating device generating a reference pulse of a given pulse height for a given period of time when the radiation pulse is higher than the initial threshold; and
an increment-threshold outputting device outputting to the comparator an increment-threshold as a reference voltage in response to the reference pulse, the increment threshold being increased from the initial threshold to the given pulse height for the given period of time.

7. The nuclear medicine diagnosis apparatus according to claim 6, wherein
the reference-pulse generating device having a capacitor and a resistor is a one-shot multivibrator circuit for generating a reference pulse of a given pulse height with a given time constant using output signals as a trigger that are outputted from the comparator, and
the increment-threshold outputting device is a CR circuit formed of a capacitor and a resistor, and increases the increment threshold with a given time constant by starting charge in response to the reference pulse.

8. The nuclear medicine diagnosis apparatus according to claim 7, further comprising:
an increment-threshold decreasing device decreasing the increment threshold to the initial threshold through discharging the capacitor forcibly; and
a threshold switching device switching between the increment-threshold outputting device and the increment-threshold decreasing device, wherein
the threshold switching device switches to the increment-threshold outputting device in synchronization with rise of the reference pulse, and switches to the increment-threshold decreasing device in synchronization with fall of the reference pulse.

9. The nuclear medicine diagnosis apparatus according to claim 7, wherein
the radiation detector has a plurality of detector cells being arranged that are formed of scintillator elements and photoelectric transducers, and
each detector cell has the comparator, the reference-pulse generating device, and the increment-threshold outputting device being arranged.

10. The nuclear medicine diagnosis apparatus according to claim 7, wherein
the nuclear medicine diagnosis apparatus is a gamma camera that uses radiopharmaceutical labeled with radioisotope that emits a single photon, and varies at least one of a time constant used for the reference pulse generating device and a time constant used for the increment-threshold outputting device in accordance with intensity of the single photon.

11. The nuclear medicine diagnosis apparatus according to claim 7, wherein
the nuclear medicine diagnosis apparatus varies at least one of a time constant used for the reference pulse generating device and a time constant used for the increment-threshold outputting device in accordance with a counting rate of the radiation pulse.

* * * * *